Figure 5:
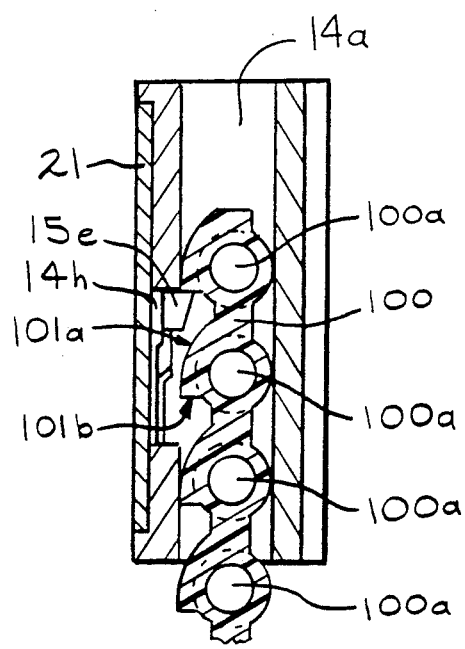

United States Patent [19]

Prindle et al.

[11] Patent Number: 4,988,335
[45] Date of Patent: Jan. 29, 1991

[54] PELLET IMPLANTER APPARATUS

[75] Inventors: Gordon E. Prindle, Schaumburg; Thomas J. Kelm, Forest Park, both of Ill.

[73] Assignee: Ideal Instruments, Inc., Chicago, Ill.

[21] Appl. No.: 232,693

[22] Filed: Aug. 16, 1988

[51] Int. Cl.$^5$ ............................................. A61M 31/00
[52] U.S. Cl. ......................................... 604/61; 604/62; 227/67
[58] Field of Search ............. 128/329 R, 330; 604/57, 604/59-64, 208, 209, 241, 243; 221/78, 79, 81, 88, 197, 198, 279; 206/3, 343, 528, 538; 124/45, 51; 606/117, 185, 188; 227/67

[56] References Cited

U.S. PATENT DOCUMENTS

| | | |
|---|---|---|
| 3,774,607 | 11/1973 | Schmitz ................................. 604/61 |
| 4,004,565 | 1/1977 | Fischer et al. . |
| 4,077,406 | 3/1978 | Sandhage et al. . |
| 4,403,610 | 9/1983 | Lodge et al. . |
| 4,447,223 | 5/1984 | Kaye et al. . |
| 4,531,938 | 7/1985 | Kaye et al. . |
| 4,553,688 | 11/1985 | Furutsu ................................. 227/67 |
| 4,576,591 | 3/1986 | Kaye et al. ........................... 604/241 |
| 4,610,384 | 9/1986 | Duchin ................................. 227/67 |
| 4,664,306 | 5/1987 | Levy ..................................... 227/67 |
| 4,681,248 | 7/1987 | Duchin ................................. 227/67 |
| 4,819,885 | 4/1989 | Satoh et al. ........................... 227/67 |

Primary Examiner—C. Fred Rosenbaum
Assistant Examiner—William W. Lewis
Attorney, Agent, or Firm—Ian C. McLeod

[57] ABSTRACT

An implanting gun apparatus (10) is described. A rod (31) is linearly moveable in a pistol grip (11) so as to move a pellet out a barrel (13). A pivotable linkage (34) between a trigger (36) and a holder (32) for the rod is actuated by the trigger. The gun apparatus is particularly adapted to implant pellets in animals, particularly as medicament pellets.

6 Claims, 3 Drawing Sheets

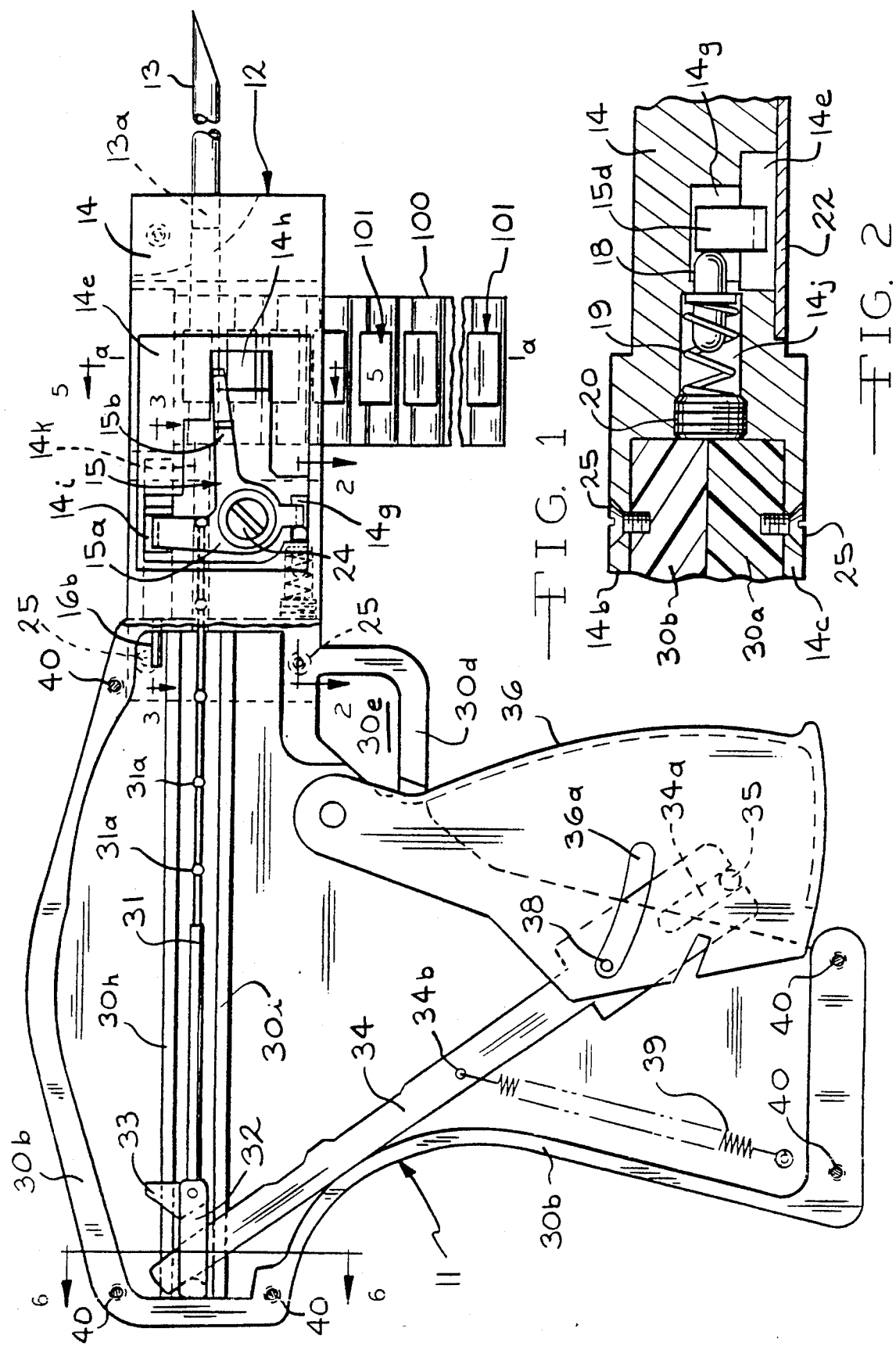

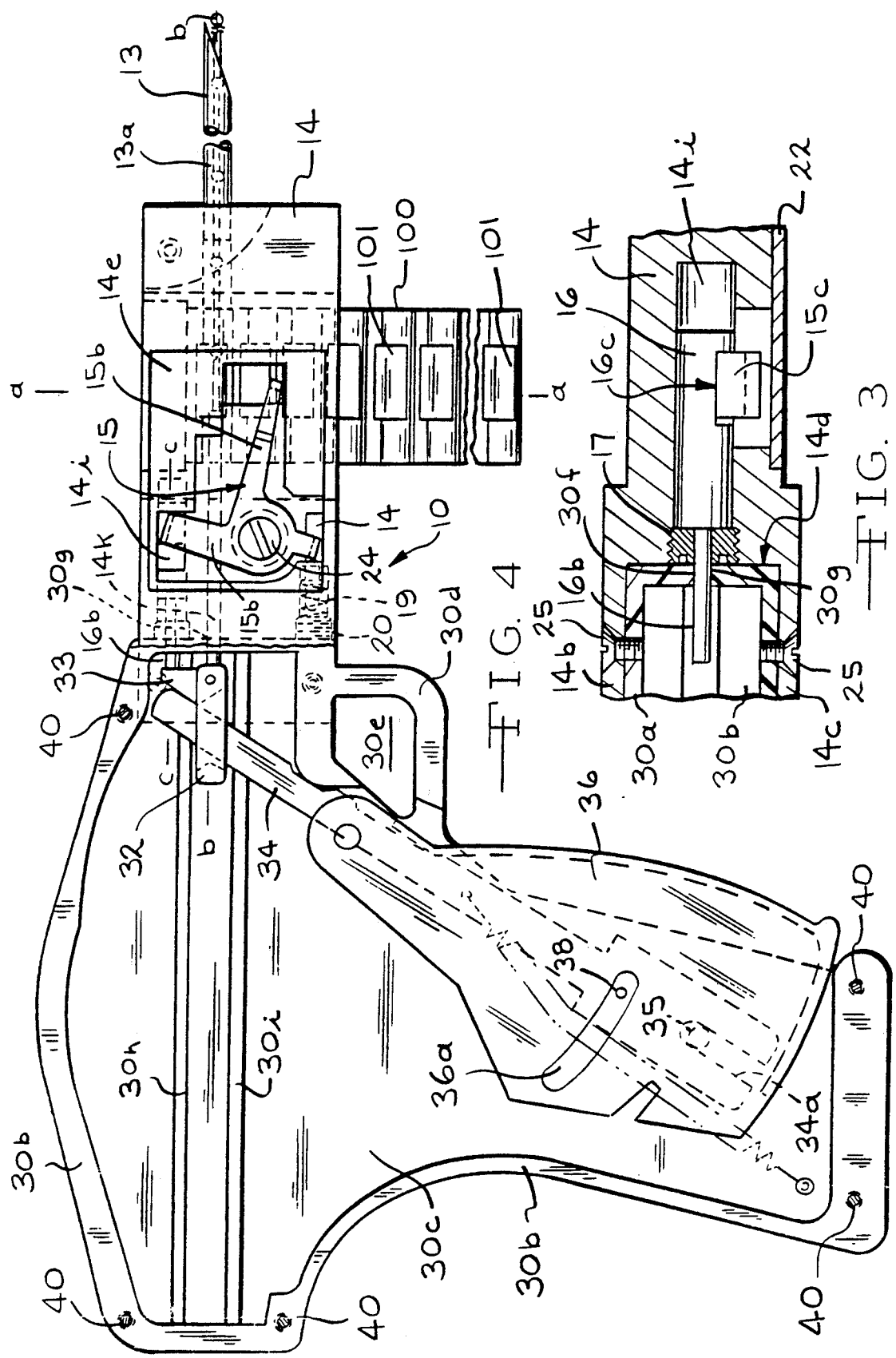

PELLET IMPLANTER APPARATUS

BACKGROUND (1) Field of the Invention

The present invention relates to a carrier fed pellet implanting apparatus for animals and the like. In particular the present invention relates to an automatic gun apparatus for implanting pellets which uses a trigger actuated linkage.

(2) Prior Art

The prior art has described hand held pellet implanting gun apparatus. The closest prior art is believed to be U.S. Pat. Nos. 4,077,406 to Sandhage et al; U.S. Pat. No. 4,403,610 to Lodge et al; and U.S. Pat. No. 4,447,223 to Kaye et al. Sandhage et al describe a non-automatic clip fed gun apparatus wherein the clip or pellet carrier is manually advanced in the gun. A spring detent 42 holds the clip and locates openings containing the pellets adjacent the barrel of a needle for implanting by movement of a trigger controlled rod 27. Lodge et al describe an automatic clip or carrier fed gun apparatus. In this apparatus, the clip is advanced by rods 24 on both sides of a carrier or magazine 12 which engage the underside of projections 25 on both sides of the magazine 12. A ball 32 detent engages a recess in the magazine 12 to hold it in place to prevent movement of the clip in the wrong direction. The construction of the gun and the magazine 12 with projections 24 requires considerable precision in order for the gun apparatus to function. Kaye et al describeds a similar carrier advancing mechanism to Lodge et al. A cam 122 serves to move the clip or carrier for the pellets. The Kaye et al device has a retractable needle and would be relatively expensive to construct because of the precision required for the cam and the carrier. U.S. Pat. Nos. 4,004,565 to Fischer and 4,531,938 to Kaye et al describe cartridge type apparatus which are more remote from the present invention.

OBJECTS

It is therefore an object of the present invention to provide a simply constructed, reliable carrier fed gun apparatus for implanting pellets. Further it is an object of the present invention to provide an inexpensive gun apparatus for implanting the pellets. These and other objects will become increasingly apparent by reference to the following description and the drawings.

IN THE DRAWINGS

FIG. 1 is a front cross-sectional view of a pellet implanting gun apparatus 10 wherein a trigger 36 and lever 15 are in their rest positions.

FIG. 2 is a plan partial cross-sectional view along line 2—2 of FIG. 1 wherein a return spring 19 and pusher pin 18 are provided for the lever arm 15.

FIG. 3 is a plan partial cross-sectional view along line 3—3 of FIG. 1 wherein an actuator 16 is shown in engagement with the lever arm 15.

FIG. 4 is a front cross-sectional view of the pellet implanting gun apparatus 10 of FIG. 1 wherein the trigger 36 is depressed and the lever 15 is in a "cocked" position adjacent a cam 101 on carrier 100.

FIG. 5 is a right end cross-sectional view along line 5—5 of FIG. 1 showing the carrier 100 and cam 101 with the lever arm 15 engaging an actuating surface 101b of the cam 101.

Figure 6:
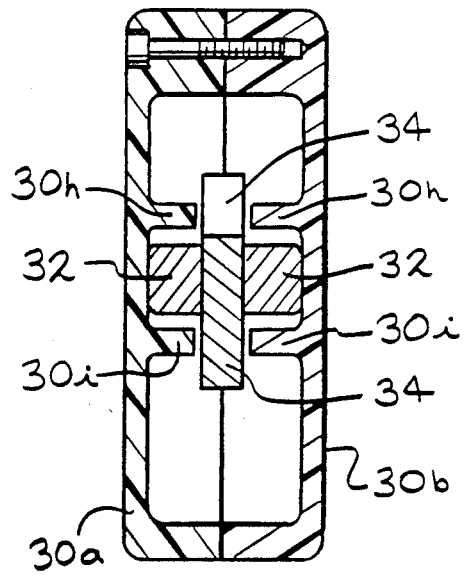

FIG. 6 is a right end cross-sectional view along line 6—6 of FIG. 1 showing a linkage member located in an opening 32a of a rod holder 31.

Figure 7:
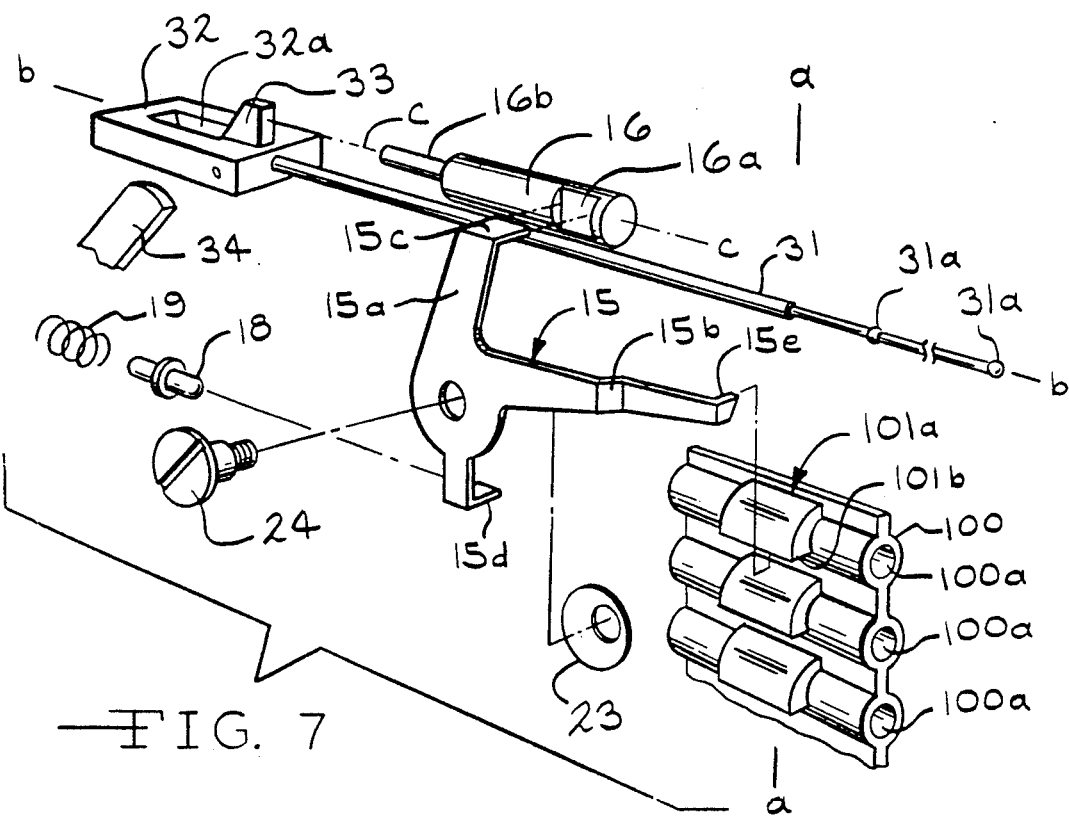

FIG. 7 is a disassembled isometric view showing the relationship of the lever arm 15, rod 31, actuator 16 pusher pin 18 and cams 101a on cam 100.

GENERAL DESCRIPTION

The present invention relates to a hand held gun apparatus for implanting a pellet into an animal which comprises: a hollow needle defining a barrel for implanting the pellet into the animal; a head means on the gun apparatus supporting the needle with an opening through the assembly into the barrel; a carrier for a pellet mounted at the opening for holding the pellet in the opening so that the pellet can pass through the barrel; a pistol grip means supporting the head means; a drive rod linearly moveable through an opening between the ends of the head means and into the barrel from the pistol grip; an actuating means mounted in the pistol grip for moving the drive rod into and out of the barrel; and trigger means mounted on the pistol grip actuatable by the hand for moving the actuating means and thus drive rod into and out of the barrel.

In particular the present invention relates to a hand held gun apparatus for implanting a pellet into an animal which comprises: a hollow needle defining a barrel for implanting the pellet into the animal; a head assembly supporting the needle at a first end and having a second end opposite the first end traversed by an opening into the barrel; a carrier for multiple pellets mounted at the opening for holding the pellet in the opening so that one of the pellets can pass through the barrel; a pistol grip attached to the head assembly at the second end; a drive rod linearly moveable from the pistol grip through the opening between the ends of the head assembly and into the barrel so as to move the pellet through the needle; an actuating means mounted inside of the pistol grip for moving the drive rod into and out of the barrel; and trigger means mounted on the pistol grip actuatable by the hand for moving the actuating means and thus the drive rod into and out of the barrel.

Thus the present invention relies upon a pivotable lever to hold and to move the carrier in the automatic gun apparatus. The lever is actuated or "cocked" upon movement of the trigger and the carrier is advanced upon release of the trigger.

SPECIFIC DESCRIPTION

FIGS. 1 to 7 show the gun apparatus 10 of the present invention. In its preferred form it includes a handle assembly 11 and head assembly 12.

The head assembly 12 has a needle 13 with a barrel 13a at one end of a body 14. The body 14 includes a slot 14a (FIG. 5 for movement of a carrier 100 along axis a—a. The head assembly 12 connects to the handle assembly 11 by means of flanges 14b and 14c and bolts 25 between the flanges 14b and 14c through the head assembly 12 in recess 14d. A recess 14e is provided for supporting a lever 15 for pivotable movement. The lever 15 includes a bar 15a and an arm 15b extending from the bar 15a. The ends of the bar 15a have extensions 15c and 15d which extend into slots 14f and 14g of the body 14 (FIGS. 2 and 3). The lever 15 is secured to the body 14 by means of a shoulder screw 24 held in place by wave spring 23 which allows slight movement of the lever 15 outward from the body 14. The arm 15b extends away from the bar 15a and has a projection 15e extending into slot 14h and extending into slot 14a. The body 14 includes holes 14i and 14j leading to slots 14f and 14g.

As shown in FIG. 3, an actuator 16 is provided in hole 14i such that slot 15a engages projection 15c from the lever 14. The actuator 16 is held in place by set screw 17 in body 14. An extension 16b of the actuator 16 extends away from the body 14. As shown in FIG. 2, a pusher pin 18 is provided in hole 14j which engages projection 15d of lever 15. The pusher pin 18 is biased by a spring 19 which is held in place by set screw 20.

Thus in operation of the head assembly 12, the extension 16b of actuator 16 can be pushed so that slot 16a engages projection 15c and moves the lever 15 clockwise on the shoulder screw 24. The bar 15a compresses spring 19, thus loading the lever 15. As the bar 15a pivots clockwise, the arm 15b also pivots in slot 14h such that projection 15d moves over the arcuate surface 101a of cam 101 on carrier 100 and snaps into place adjacent a radial drive surface 101b. When the pressure on the extension 16b of the actuator 16 is released, the lever arm 15 is pivoted counter-clockwise back to its starting position by spring 19 and extension 15e pushes the radial drive surface 101b of cam 101. Thus moving the carrier 100 upwards along axis a—a to index another opening 100a of carrier 100 between opening 14k leading to barrel 13a. Generally cover plates 21 and 22 cover the slot 14a and opening 14e in use. The handle assembly 11 is used to actuate the lever 15 by means of the extension 16b.

The handle assembly 11 includes a right half 30a and a left half 30b which are mirror images of each other. The halves 30a and 30b have a grip portion 30c and a trigger ring 30d defined by opening 30e. The front of the halves 30a and 30b are provided with two semi-circular grooves 30f and 30g. The upper opening 30f receives the extension 16b. The lower opening 30g receives a drive rod 31 which has an axis in line with the opening 14k and barrel 13a along axis b—b. Rounded portions 31a of rod 31 slide in opening 14k and barrel 13a and reduce friction because of limited surface contact.

The rod 31 is moved between parallel side rails 30h and 30i on each half 30a and 30b of the handle assembly 11 by a rod holder 32 which slides between the rails 30h and 30i. A pusher 33 extends above the rails 30h to a height corresponding to axis c—c of the actuator 16 and extension 16a. When the rod 31 is moved in rails 30h and 30i, the pusher 33 engages the extension 16b of the actuator to depress it in the head assembly 12.

A linkage member 34 extends into an opening 32a in the holder 32 and is connected to a trigger 36. The trigger 36 is pivoted on pin 37 mounted on one of the halves 30a and 30b. The linkage member 34 has a slot 34a which slides roller bearing 35 on trigger 36. The linkage member is pivoted on pin 38 on trigger 36 which rotates in an arc in slot 36a of the trigger 36. Spring 39 is connected to the bottom of grip 30c and to a midpoint of the linkage member 34 in opening 34b. The halves 30a and 30b are held together by screws 40.

In operation as best seen from FIG. 7, when the trigger 36 is depressed inside the handle assembly 11 the roller bearing slides 35 in slot 34a to pivot the linkage member 34 on pin 38 against the tension of the spring 39. The linkage member 34 thus moves the rod holder 32 and rod 31 out of the handle assembly 11 through the opening 100a in clip or carrier 100, out the barrel 13a on needle 13 to implant a pellet. At the same time, the pusher 33 engages the extension 16a of actuator 16 to move the lever 15 and projection 15e of arm 15b over the arcuate surface 101a of cam 101 so that it snaps into place adjacent radial drive surface 101b. When the trigger 36 is released the carrier is moved by projection 15e engaging the drive surface 101b to move the carrier 100 upwards to align a new opening 100a. Each time the trigger is pulled, a new opening 100a is presented between the rod 31 and the barrel 13a of the needle 13 for injection.

It will be appreciated that the various actuating means can be used to connect the drive rod 31 and the trigger 36. Further, various means can be used for actuating lever 15 as a function of movement of the rod 15. Primarily the need is to rotate and cock the lever 15 so that a drive surface 101b is engaged as the trigger 36 is depressed and then to move the carrier 100 when the trigger 36 is released.

It will be appreciated that various carriers and cam designs can be used, although the clip or carrier 10 and cam 101 design of FIG. 7 is preferred. All that is required is that the rotating lever 15 be able to move the carrier 100.

Numerous variations will occur to those skilled in the art and it is intended that the present invention be limited only to the hereinafter appended claims.

I claim:

1. A hand held gun apparatus for implanting a pellet into an animal which comprises:
   (a) a hollow needle defining a barrel for implanting the pellet into the animal;
   (b) a head means on the gun apparatus supporting the needle with an opening through the head means into the barrel;
   (c) a carrier for a pellet mounted at the opening for holding the pellet in the opening so that the pellet can pass through the barrel;
   (d) a pistol grip means supporting the head means;
   (e) a drive rod linearly moveable through an opening between the ends of the head means and into the barrel from the pistol grip;
   (f) an actuating means mounted in the pistol grip for moving the drive rod into and out of the barrel; and
   (g) trigger means mounted on the pistol grip and having opposed sides which slide into the pistol grip and actuatable by the fingers for moving the actuating means and thus drive rod into and out of the barrel, wherein the actuating means is a pivotable linkage means mounted on a pivot means on the pistol grip adjacent the trigger means and between linearly movable holder means for the drive rod and an inside portion of the trigger means, wherein there are arcuate openings on the opposed sides of the trigger means which are movable over the pivot means when the trigger means is moved into the pistol grip, wherein a spring means is mounted between the pistol grip and linkage means to return the linkage means and the trigger means to a rest position after the trigger means is released from being moved into the pistol grip, wherein the linkage means, holder means and drive rod are moved by movement of a surface of the linkage means on a roller bearing mounted on the inside portion of the trigger means and wherein the linearly movable holder means for the rod is mounted in a slot in the pistol grip and the holder means with the rod is moved by the linkage means in the slot and wherein the linkage means passes through and out of an opening in the holder means and pushes the holder means as the trigger means is actuated to move the holder means and rod so that the rod is moved into the barrel of the needle.

2. A hand held gun apparatus for implanting a pellet into an animal which comprises:
   (a) a hollow needle defining a barrel for implanting the pellet into the animal;
   (b) a head assembly supporting the needle at a first end and having a second end opposite the first end traversed by an opening into the barrel;
   (c) a carrier for multiple pellets mounted at the opening for holding the pellet in the opening so that one of the pellets can pass through the barrel;
   (d) a pistol grip attached to the head assembly at the second end;
   (e) a drive rod linearly movable from the pistol grip through the opening between the ends of the head assembly and into the barrel;
   (f) an actuating means mounted inside of the pistol grip for moving the drive rod into and out of the barrel; and
   (g) trigger means mounted on the pistol grip and having opposed sides which slide into the pistol grip actuatable by the fingers for moving the actuating means and thus the drive rod into and out of the barrel, wherein the actuating means is a pivotable linkage means mounted on pivot means on the pistol grip adjacent the trigger means and between a linearly moveable holder means for the drive rod and an inside portion of the trigger means, wherein there are arcuate openings on the opposed sides of the trigger means which are movable over the pivot means when the trigger is moved into the pistol grip, wherein a spring means is mounted between the pistol grip and linkage means to return the linkage means and the trigger means to rest position after the trigger means is released from being moved into the pistol grip and wherein the linkage means and drive rod are moved by movement of a surface of the linkage means on a roller bearing mounted on the inside portion of the trigger means and wherein the linearly moveable holder means for the rod is mounted in a slot in the pistol grip and the holder with the rod is moved by the linkage means in the slot and wherein the linkage means passes through and out of an opening in the holder means as the trigger means is actuated to move the holder means and rod so that the rod is moved into the barrel of the needle.

3. The apparatus of claim 2 wherein the head assembly is attached to the pistol grip by means of screws through spaced apart flanges on the head assembly at the second end.

4. The apparatus of claim 2 wherein the trigger means is pivoted on a first pin mounted on the pistol grip adjacent to the head means.

5. A hand held gun apparatus for implanting a pellet into an animal which comprises:
   (a) a hollow needle defining a barrel for implanting the pellet into the animal;
   (b) a head means on the gun apparatus supporting the needle with an opening through the head means into the barrel;
   (c) a carrier for a pellet mounted at the opening for holding the pellet in the opening so that the pellet can pass through the barrel;
   (d) a pistol grip means supporting the head means;
   (e) a drive rod linearly moveable through an opening between the ends of the head means and into the barrel from the pistol grip;
   (f) an actuating means mounted in the pistol grip for moving the drive rod into and out of the barrel; and
   (g) trigger means mounted on the pistol grip and having opposed sides which slide into the pistol grip and actuatable by the fingers for moving the actuating means and thus drive rod into and out of the barrel, wherein the actuating means is a pivotable linkage means mounted on a pivot means on the pistol grip adjacent the trigger means and between the drive rod and an inside portion of the trigger means, wherein there are openings on the opposed sides of the trigger means which are movable over the pivot means when the trigger means is moved into the pistol grip, wherein a spring means is mounted between the pistol grip and linkage means to return the linkage means and the trigger means to a rest position after the trigger means is released from being moved into the pistol grip, wherein the linkage means and drive rod are moved by movement of a surface of the linkage means on a roller bearing mounted on the inside portion of the trigger means and wherein a linearly moveable holder means for the rod is mounted in a slot in the pistol grip and the holder means with the rod is moved by the linkage means in the slot, wherein the head means is attached to the pistol grip by means of screws through spaced apart flanges on the head means.

6. A hand held gun apparatus for implanting a pellet into an animal which comprises:
   (a) a hollow needle defining a barrel for implanting the pellet into the animal;
   (b) a head assembly supporting the needle at a first end and having a second end opposite the first end traversed by an opening into the barrel;
   (c) a carrier for multiple pellets mounted at the opening for holding the pellet in the opening so that one of the pellets can pass through the barrel;
   (d) a pistol grip attached to the head assembly at the second end;
   (e) a drive rod linearly moveable from the pistol grip through the opening between the ends of the head assembly and into the barrel;
   (f) an actuating means mounted inside of the pistol grip for moving the drive rod into and out of the barrel; and
   (g) trigger means mounted on the pistol grip and having opposed sides which slide into the pistol grip actuatable by the fingers for moving the actuating means and thus the drive rod into and out of the barrel, wherein the actuating means is a pivotable linkage means mounted on pivot means on the pistol grip adjacent the trigger means and between the drive rod and an inside portion of the trigger means, wherein there are openings on the opposed sides of the trigger means which are movable over the pivot means when the trigger means is moved into the pistol grip, wherein a spring means is mounted between the pistol grip and linkage means to return the linkage means and the trigger means to a rest position after the trigger means is released from being moved into the pistol grip and wherein the linkage means and drive rod are moved by movement of a surface of the linkage means on a roller bearing mounted on the inside portion of the trigger means and wherein a linearly moveable holder means for the rod is mounted in a slot in the pistol grip and the holder means with the rod is moved by the linkage means in the slot, wherein the head assembly is attached to the pistol grip by means of screws through spaced apart flanges on the head assembly at the second end.

* * * * *

UNITED STATES PATENT AND TRADEMARK OFFICE
CERTIFICATE OF CORRECTION

PATENT NO. : 4,988,335

DATED : January 29, 1991

INVENTOR(S) : Gordon E. Prindle and Thomas J. Kelm

It is certified that error appears in the above-identified patent and that said Letters Patent is hereby corrected as shown below:

In the Drawings, "14" should be added in Figure 4.

Column 1, line 32, "describeds" should be --describes--.

Column 2, line 55, "(Fig. 5" should be --(Fig. 5)--.

Column 3, line 5, "slot 15a" should be --slot 16a--.

Column 3, line 6, "lever 14" should be --lever 15--.

Column 3, line 18, "15d" should be --15e--.

Column 3, line 55, "slides roller bearing" should read --slides on a roller bearing--.

Column 3, line 56, after "member", the number --34-- should be inserted.

Column 3, line 63, "bearing slides 35" should read --bearing 35 slides--.

UNITED STATES PATENT AND TRADEMARK OFFICE
CERTIFICATE OF CORRECTION

PATENT NO. : 4,988,335

DATED : January 29, 1991

INVENTOR(S) : Gordon E. Prindle and Thomas J. Kelm

It is certified that error appears in the above-identified patent and that said Letters Patent is hereby corrected as shown below:

Column 4, line 5, after carrier, the number --100-- should be inserted.

Column 4, line 14, "rod 15" should be --rod 31--.

Column 4, line 33, after "opening" the following should be inserted --between opposed ends of and--.

Column 4, line 40, after "between the" the following should be inserted --opposed ends of and between the ends of--.

Column 5, line 37, before "rest" insert --a--.

Signed and Sealed this

Twenty-seventh Day of October, 1992

Attest:

DOUGLAS B. COMER

*Attesting Officer*  *Acting Commissioner of Patents and Trademarks*